United States Patent
Choi et al.

(10) Patent No.: US 11,419,529 B2
(45) Date of Patent: Aug. 23, 2022

(54) APPARATUS AND METHOD FOR MEASURING BIO-SIGNAL

(71) Applicant: SAMSUNG ELECTRONICS CO., LTD., Suwon-si (KR)

(72) Inventors: Chang Mok Choi, Suwon-si (KR); Byung Hoon Ko, Hwaseong-si (KR); Jong Wook Lee, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 396 days.

(21) Appl. No.: 16/748,342

(22) Filed: Jan. 21, 2020

(65) Prior Publication Data

US 2020/0229743 A1 Jul. 23, 2020

(30) Foreign Application Priority Data

Jan. 23, 2019 (KR) .................. 10-2019-0008609

(51) Int. Cl.
*A61B 5/1455* (2006.01)
*A61B 5/00* (2006.01)
(Continued)

(52) U.S. Cl.
CPC ...... *A61B 5/14552* (2013.01); *A61B 5/02108* (2013.01); *A61B 5/681* (2013.01);
(Continued)

(58) Field of Classification Search
CPC . A61B 5/0205; A61B 5/1455; A61B 5/14551; A61B 5/14552; A61B 5/14532;
(Continued)

(56) References Cited

U.S. PATENT DOCUMENTS 6,334,065 B1 * 12/2001 Al-Ali .................. A61B 5/0205
600/323
6,503,206 B1 * 1/2003 Li ...................... A61B 5/02125
600/300
(Continued)

FOREIGN PATENT DOCUMENTS

JP 2012-024320 A 2/2012
KR 10-1560521 B1 10/2015
(Continued)

OTHER PUBLICATIONS

Radovan Stojanovic and Dejan Karadaglic, "Design of an Oximeter Based on LED-LED Configuration and FPGA Technology", Sensors 2013, 13, 574-586 (13 pages total).
(Continued)

*Primary Examiner* — Chu Chuan Liu
(74) *Attorney, Agent, or Firm* — Sughrue Mion, PLLC

(57) ABSTRACT

An apparatus for estimating bio-information of an object of interest may include a processor configured to obtain a plurality of pulse wave signals of an object via a plurality of channels, determine a plurality of oxygen saturation values corresponding to the plurality of channels based on the plurality of pulse wave signals, select a channel to be used for estimating the bio-information of the object of interest from among the plurality of channels based on the plurality of oxygen saturation values, and estimate the bio-information of the object of interest based on a pulse wave signal corresponding to the selected channel.

20 Claims, 11 Drawing Sheets

(51) Int. Cl.
*A61B 5/021* (2006.01)
*A61B 5/029* (2006.01)
*A61B 5/02* (2006.01)
*A61B 5/145* (2006.01)
*A61B 5/024* (2006.01)

(52) U.S. Cl.
CPC .......... *A61B 5/6843* (2013.01); *A61B 5/7278* (2013.01); *A61B 5/02007* (2013.01); *A61B 5/029* (2013.01); *A61B 5/02433* (2013.01); *A61B 5/14532* (2013.01); *A61B 2562/0238* (2013.01); *A61B 2562/043* (2013.01)

(58) Field of Classification Search
CPC ..... A61B 5/681; A61B 5/6843; A61B 5/7278; A61B 5/02108; A61B 5/029; A61B 5/02007; A61B 5/02433; A61B 5/02; A61B 2562/0238; A61B 2562/043
See application file for complete search history.

(56) References Cited

U.S. PATENT DOCUMENTS

| 2010/0130876 | A1* | 5/2010 | Cho | A61B 5/681 600/490 |
|---|---|---|---|---|
| 2012/0046532 | A1* | 2/2012 | Chang | A61B 5/14552 600/479 |
| 2014/0275825 | A1* | 9/2014 | Lisogurski | A61B 5/14552 600/323 |
| 2015/0282746 | A1 | 10/2015 | Yousefi et al. | |
| 2016/0361004 | A1 | 12/2016 | Lange et al. | |
| 2016/0361029 | A1 | 12/2016 | Kang et al. | |
| 2017/0007136 | A1 | 1/2017 | Gil | |
| 2017/0049404 | A1 | 2/2017 | Azarnasab et al. | |
| 2019/0076032 | A1 | 3/2019 | Park et al. | |
| 2020/0015690 | A1 | 1/2020 | Choi et al. | |

FOREIGN PATENT DOCUMENTS

| KR | 10-2016-0146393 A | 12/2016 |
|---|---|---|
| KR | 10-2018-0078921 A | 7/2018 |
| KR | 10-2019-0030152 A | 3/2019 |
| KR | 10-2020-0007503 A | 1/2020 |
| KR | 10-2020-0054723 A | 5/2020 |

OTHER PUBLICATIONS

Kristen M. Warren et al., "Improving Pulse Rate Measurements during Random Motion Using a Wearable Multichannel Reflectance Photoplethysmograph", Sensors 2016, 16, 342, pp. 1-18 (18 pages total).

V.O. Rybynok and P.A. Kyriacou, "Theory of Dynamic Pulsatile Spectroscopy for Photoplethysmographic Signals Analysis",35th Annual International Conference of the IEEE Engineering-in-Medicine-and-Biology-Society (EMBS), 2013, (5 pages total).

Jermana L. Moraes et al., "Advances in Photopletysmography Signal Analysis for Biomedical Applications", Sensors 2018, 18, 1894, pp. 1-26 (26 pages total).

* cited by examiner

APPARATUS AND METHOD FOR MEASURING BIO-SIGNAL

CROSS-REFERENCE TO RELATED APPLICATION(S)

This application is based on and claims priority under 35 U.S.C. § 119 to Korean Patent Application No. 10-2019-0008609, filed on Jan. 23, 2019, in the Korean Intellectual Property Office, the disclosure of which is incorporated by reference herein in its entirety.

BACKGROUND

1. Field

The disclosure relates to an apparatus and method for measuring a bio-signal.

2. Description of Related Art

Healthcare technology has attracted much attention due to the rapid entry into an aging society and relevant social problems such as increases in medical expenses. Accordingly, medical devices that can be utilized by hospitals and inspection agencies and also small-sized medical devices that can be carried by individuals are being developed. In addition, such a small-sized medical device is worn by a user in the form of a wearable device capable of directly measuring the user's bio-information, such as blood pressure, which enables the user to directly measure and manage the bio-information.

Therefore, research regarding miniaturization of a device and a method of accurately estimating bio-information using a pulse wave has been actively conducted.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Additional aspects will be set forth in part in the description which follows and, in part, will be apparent from the description, or may be learned by practice of the presented embodiments.

The disclosure relates to an apparatus and method for measuring a bio-signal.

According to an aspect of the disclosure, an apparatus for estimating bio-information of an object of interest may include a processor configured to obtain a plurality of pulse wave signals of an object via a plurality of channels, determine a plurality of oxygen saturation values corresponding to the plurality of channels based on the plurality of pulse wave signals, select a channel to be used for estimating the bio-information of the object of interest from among the plurality of channels based on the plurality of oxygen saturation values, and estimate the bio-information of the object of interest based on a pulse wave signal corresponding to the selected channel.

The apparatus may include a pulse wave sensor comprising one or more light source assemblies each configured to emit light of at least two different wavelengths toward the object of interest, and two or more photodetectors configured to measure the plurality of pulse wave signals by receiving light reflected by the object of interest.

The apparatus may include a pulse wave sensor comprising two or more light source assemblies each configured to emit light of at least two different wavelengths toward the object of interest, and one or more photodetectors configured to measure the plurality of pulse wave signals by receiving light reflected by the object of interest.

Each of the plurality of channels may include a light source assembly configured to emit light of at least two different wavelengths toward the object of interest and a photodetector configured to measure the plurality of pulse wave signals by receiving light reflected by the object of interest.

The at least two wavelengths may include a red wavelength and an infrared wavelength.

The processor may determine an alternating current (AC) component and a direct current (DC) component of each of the plurality of pulse wave signals, and determine the plurality of oxygen saturation values corresponding to the plurality of channels based on the determined AC component and DC components.

The processor may determine, for each channel, a point at which an amplitude of a respective pulse wave signal is maximum, and select, as the channel to be used for estimating the bio-information, the channel in which a decrease of oxygen saturation occurs from the determined point for a predetermined period of time and in which an amount of decrease in oxygen saturation is the greatest from among the plurality of channels.

The processor may determine, for each channel, a point at which an amplitude of a respective pulse wave signal is maximum, and select, from among the plurality of channels, the channel having the greatest oxygen saturation within a predetermined time interval associated with the determined point as the channel to be used for estimating the bio-information.

The apparatus may include a pressure sensor configured to measure a contact pressure signal corresponding to a contact pressure between the object of interest and a pulse wave sensor. The processor may determine a time interval that corresponds to a predetermined contact pressure interval based on the measured contact pressure signal, and select, from among the plurality of channels, the channel having the greatest oxygen saturation within the time interval as the channel to be used for estimating the bio-information.

The apparatus may include a pressure sensor configured to measure a contact pressure signal corresponding to a contact pressure between the object of interest and a pulse wave sensor. The processor may generate guide information for inducing an increase or decrease of the contact pressure between the object of interest and the pulse wave sensor based on the measured contact pressure signal.

The bio-information may include at least one of blood pressure, vascular age, degree of arteriosclerosis, vascular compliance, blood sugar, blood triglyceride, cardiac output, and total peripheral resistance.

The apparatus may include a pressure sensor configured to measure a contact pressure signal corresponding to a contact pressure between the object of interest and the pulse wave sensor. The processor may estimate blood pressure of the object of interest based on the pulse wave signal corresponding to the selected channel and the measured contact pressure signal.

According to an aspect of the disclosure, a method of estimating bio-information of an object of interest may include measuring a plurality of pulse wave signals of the object of interest via a plurality of channels, determining a plurality of oxygen saturation values corresponding to the plurality of channels based on the measured plurality of pulse wave signals, selecting a channel to be used for estimating the bio-information from among the plurality of channels based on the plurality of oxygen saturation values, and estimating the bio-information of the object based on a pulse wave signal corresponding to the selected channel.

The determining of the plurality of oxygen saturation values may include determining an alternating current (AC) component and a direct current (DC) component of each of the plurality of pulse wave signals and determining the plurality of oxygen saturation values based on the determined AC component and DC components.

The selecting of the channel to be used for estimating the bio-information from among the plurality of channels may include determining, for each channel, a point at which an amplitude of a respective pulse wave signal is maximum and selecting, as the channel to be used for estimating the bio-information, the channel in which a decrease of oxygen saturation occurs from the determined point for a predetermined period of time and an amount of decrease is the greatest from among the plurality of channels.

The selecting of the channel to be used for estimating bio-information from among the plurality of channels may include determining, for each channel, a point at which an amplitude of the pulse wave signal is maximum and selecting, as the channel to be used for estimating the bio-information, the channel having the greatest oxygen saturation within a predetermined time interval associated with the determined point from among the plurality of channels.

The method may include measuring a contact pressure signal corresponding to a contact pressure between the object of interest and a pulse wave sensor. The selecting of the channel to be used for estimating the bio-information from among the plurality of channels may include determining a time interval that corresponds to a predetermined contact pressure interval based on the measured contact pressure signal and selecting the channel having the greatest oxygen saturation within the time interval from among the plurality of channels.

The method may include measuring a contact pressure signal corresponding to a contact pressure between the object of interest and a pulse wave sensor, and generating guide information for inducing an increase or decrease of the contact pressure between the object of interest and the pulse wave sensor based on the measured contact pressure signal.

The bio-information may include at least one of blood pressure, vascular age, degree of arteriosclerosis, vascular compliance, blood sugar, blood triglyceride, cardiac output, and total peripheral resistance.

The method may include measuring a contact pressure signal corresponding to a contact pressure between the object of interest and a pulse wave sensor, and estimating blood pressure of the object of interest based on the pulse wave signal measured via the selected channel and the measured contact pressure signal.

Other features and aspects will be apparent from the following detailed description, the drawings, and the claims.

BRIEF DESCRIPTION OF THE DRAWINGS

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Figure 1:
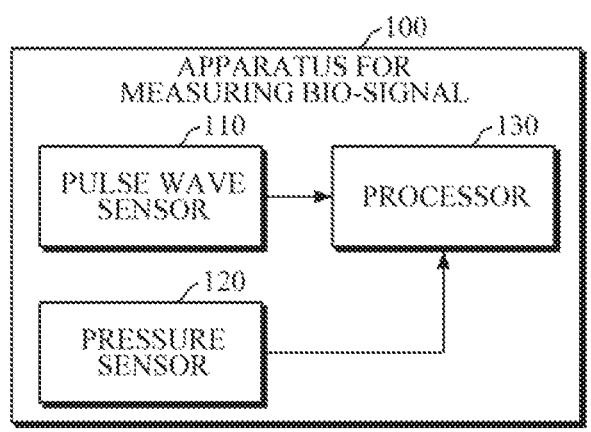
FIG. 1 is a diagram illustrating an apparatus for measuring a bio-signal according to an embodiment.

The following detailed description is provided to assist the reader in gaining a comprehensive understanding of the methods, apparatuses, and/or systems described herein. Various changes, modifications, and equivalents of the systems, apparatuses, and/or methods described herein should be apparent to those of ordinary skill in the art. In the following description, a detailed description of known functions and configurations incorporated herein may be omitted so as to not obscure the subject matter with unnecessary detail. Throughout the drawings and the detailed description, unless otherwise described, the same reference numerals may refer to the same elements, features, and structures. The relative size and depiction of these elements may be exaggerated for clarity, illustration, and convenience.

As used herein, the singular forms of terms may include the plural forms of the terms as well, unless the context clearly indicates otherwise. It should be further understood that terms such as "comprises," "comprising," "includes," "including," etc., when used in this description, specify the presence of stated features, numbers, steps, operations, elements, components, or combinations thereof, but may not preclude the presence or addition of one or more other features, numbers, steps, operations, elements, components, or combinations thereof.

It should also be understood that the elements or components in the following description are discriminated in accordance with their respective main functions. In other words, two or more elements may be integrated into a single element, or a single element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

An apparatus for measuring a bio-signal, which will be described below, may be implemented as a software module or in the form of a hardware chip and may be mounted in an electronic device. In this case, the electronic device may include a mobile phone, a smartphone, a tablet computer, a notebook computer, a personal digital assistant (PDA), a portable multimedia player (PMP), a navigation device, an MP3 player, a digital camera, a wearable device, and the like, and the wearable device may include a wrist watch type, a wrist band-type, a ring-type, a belt-type, a necklace-type, an ankle band-type, a thigh band-type, a forearm band-type, and the like. However, the electronic device and the wearable device are not limited to the above examples.

Figure 2:
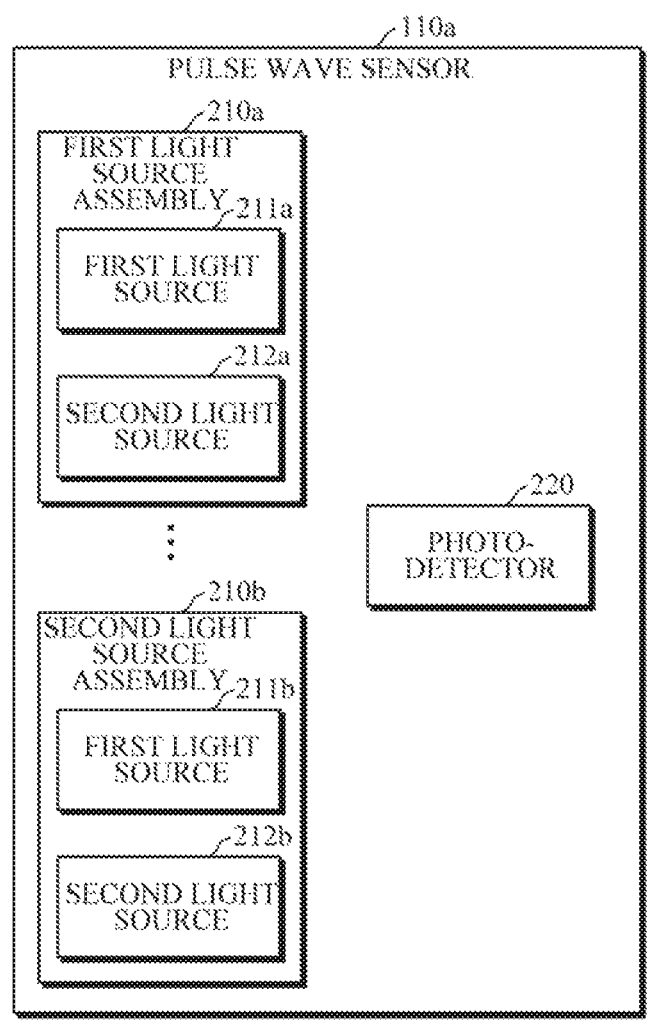
FIGS. 2 to 4 are diagrams illustrating a pulse wave measurer according to an embodiment.
Figure 3:
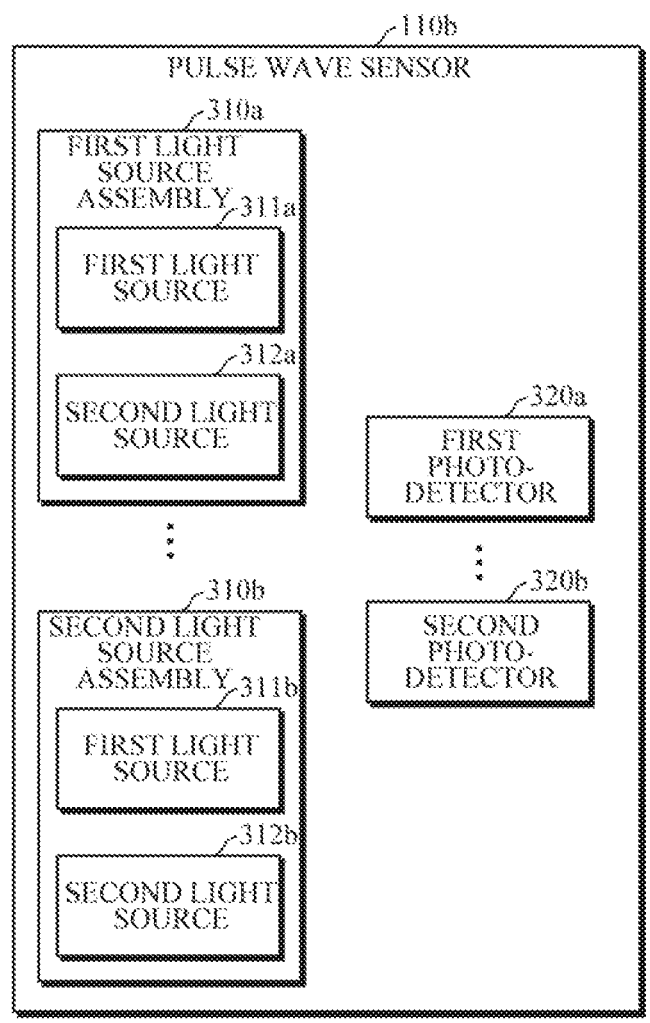
Figure 4:
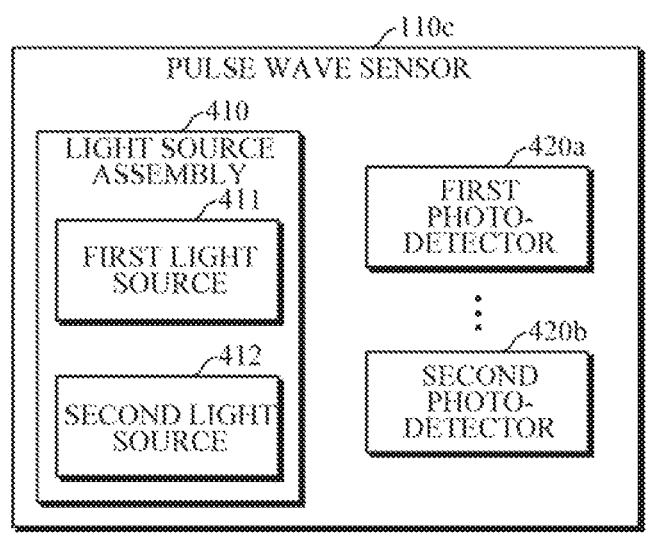
Figure 5:
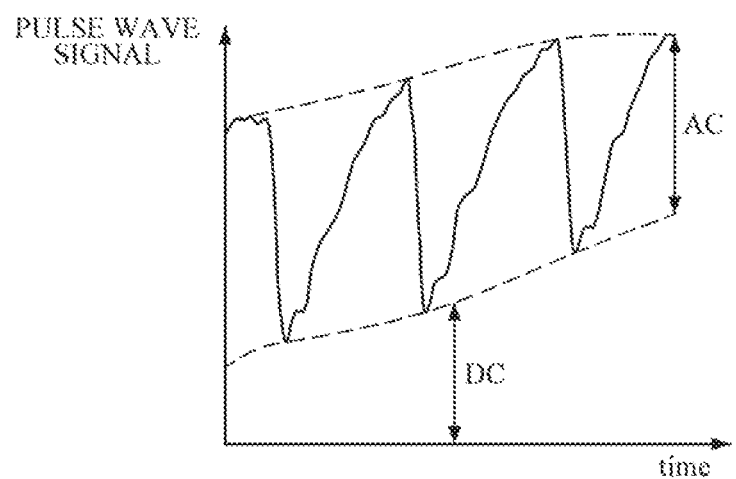
FIG. 5 is a graph showing an alternating current (AC) component and a direct current (DC) component of pulse wave components according to an embodiment.
Figure 6:
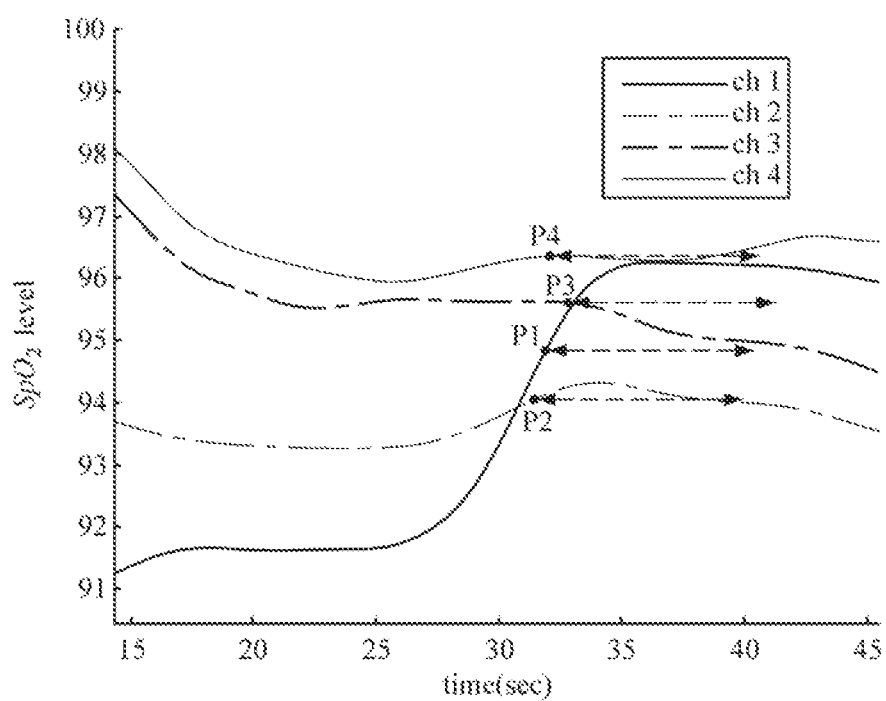
FIGS. 6 to 8 are graphs for describing a method of selecting a channel to be used in estimating bio-information from among a plurality of channels according to an embodiment.
Figure 7:
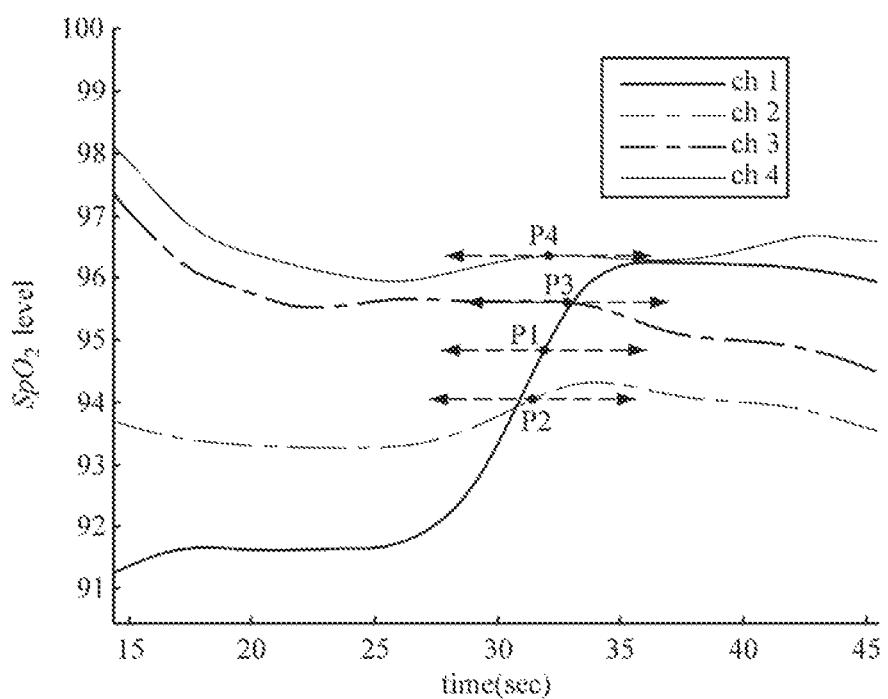
Figure 8:
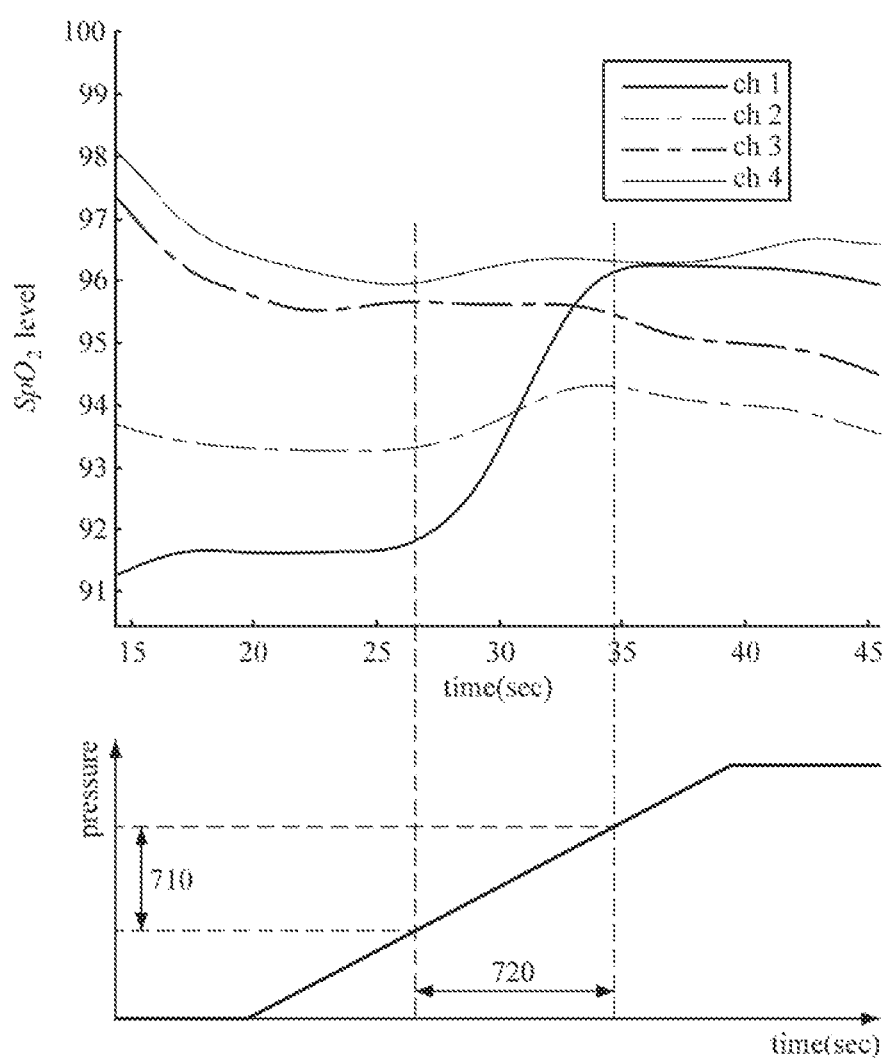

FIG. 1 is a diagram illustrating an apparatus for measuring a bio-signal according to an embodiment, FIGS. 2 to 4 are diagrams illustrating a pulse wave measurer according to an embodiment, FIG. 5 is a graph showing an alternating current (AC) component and a direct current (DC) component of pulse wave components according to an embodiment, and FIGS. 6 to 8 are graphs for describing a method of selecting a channel to be used in estimating bio-information from among a plurality of channels according to an embodiment.

Referring to FIG. 1, the apparatus 100 for measuring a bio-signal may include a pulse wave sensor 110, a pressure sensor 120, and a processor 130.

The pulse wave sensor 110 may measure a pulse wave signal of an object of interest via a plurality of channels. The pulse wave signal may be a photoplethysmogram (PPG) signal, or the like. According to an embodiment, based on the object of interest contacting the pulse wave sensor 110, the pulse wave sensor 110 may emit light toward the object of interest and measure a pulse wave signal of the object via a plurality of channels by receiving light reflected by or scattered from the object. In this case, the channel may be formed by a combination of a light source assembly and a photodetector, and the light source assembly may include at least two light sources that emit light having different wavelengths. For example, the light source assembly may include at least a red light source and an infrared light source.

The object of interest may be a body part where measurement of a pulse wave signal is relatively easier than as compared to other body parts. For example, the object of interest may be a peripheral part of the body, such as a finger, a toe, or the like, or a region of a wrist surface adjacent to the radial artery, which is an upper area of the wrist where the capillary blood or venous blood passes through.

Hereinafter, embodiments of the pulse wave sensor 110 will be described in detail with reference to FIGS. 2 to 4.

Referring to FIG. 2, the pulse wave sensor 110a according to an embodiment may include two or more light source assemblies 210a and 210b and a photodetector 220. In this case, a first light source assembly 210a and the photodetector 220 may form a first channel, and a second light source assembly 210b and the photodetector 220 may form a second channel.

The first light source assembly 210a may include a first light source 211a configured to emit light of a first wavelength toward the object of interest, and a second light source 212a configured to emit light of a second wavelength toward the object of interest. The second light source assembly 210b may include a first light source 211b configured to emit light of the first wavelength to the object of interest, and a second light source 210b configured to emit light of the second wavelength toward the object of interest. In this case, the first wavelength may be a red wavelength, and the second wavelength may be an infrared wavelength.

According to an embodiment, each of the light sources 211a, 211b, 212a, and 212b may be configured as a light emitting diode (LED), an organic light emitting diode (OLED), a quantum dot light-emitting diode (QLED), a laser diode, a phosphor, or the like, but is not limited thereto.

In FIG. 2, each of the light source assemblies 210a and 210b includes two light sources, which is merely for convenience of description, but is not limited thereto. That is, each of the light source assemblies 210a and 210b may further include one or more light sources configured to emit light of a different wavelength (e.g., blue wavelength, green wavelength, or the like) from those of the first light sources 211a and 211b and the second light sources 212a and 212b.

The photodetector 220 may measure a first pulse wave signal of the first channel by receiving light of the first wavelength reflected by the object radiated by the first light source 211a, and measure a second pulse wave signal of the first channel by receiving light of the second wavelength reflected by the object radiated by the second light source 212a. In addition, the photodetector 220 may measure a first pulse wave signal of the second channel by receiving light of the first wavelength reflected by the object radiated by the first light source 211b, and measure a second pulse wave signal of the second channel by receiving light of the second wavelength reflected by the object radiated by the second light source 212b.

According to an embodiment, the photodetector 220 may be configured with a photodiode, a phototransistor, or a charge-coupled device (CCD), but is not limited thereto.

Referring to FIG. 3, the pulse wave sensor 110b according to an embodiment may include two or more light source assemblies 310a and 310b and two or more photodetectors 320a and 320b. In this case, a first light source assembly 310a and a first photodetector 320a may form a first channel, the first light source assembly 310a and a second photodetector 320b may form a second channel, a second light source assembly 310b and the first photodetector 320a may form a third channel, and the second light source assembly 310b and the second photodetector 320b may form a fourth channel.

The first light source assembly 310a may include a first light source 311a configured to emit light of first wavelength toward an object of interest, and a second light source 312a configured to emit light of a second wavelength toward the object. The second light source assembly 310b may include a first light source 311b configured to emit light of the first wavelength toward the object, and a second light source 312b configured to emit light of the second wavelength toward the object. In this case, the first wavelength may be a red wavelength and the second wavelength may be an infrared wavelength.

In FIG. 3, each of the light source assemblies 310a and 310b includes two light sources, which is merely for convenience of description, but is not limited thereto. That is, each of the light source assemblies 310a and 310b may further include one or more light sources configured to emit light of a different wavelength (e.g., blue wavelength, green wavelength, or the like) from those of the first light sources 311a and 311b and the second light sources 312a and 312b.

The first photodetector 320a may measure a first pulse wave signal of the first channel by receiving light of the first wavelength reflected by the object of interest radiated by the first light source 311a, and measure a second pulse wave signal of the first channel by receiving light of the second wavelength reflected by the object radiated by the second light source 312a. Also, the first photodetector 320a may measure a first pulse wave signal of the third channel by receiving light of the first wavelength reflected by the object radiated by the first light source 311b, and measure a second pulse wave signal of the third channel by receiving light of the second wavelength reflected by the object radiated by the second light source 312b.

The second photodetector 320b may measure a first pulse wave signal of the second channel by receiving light of the first wavelength reflected by the object radiated by the first light source 311a, and measure a second pulse wave signal of the second channel by receiving light of the second wavelength reflected by the object radiated by the second light source 312a. In addition, the second photodetector 320b may measure a first pulse wave signal of the fourth channel by receiving light of the first wavelength reflected by the object radiated by the first light source 311b, and measure a second pulse wave signal of the fourth channel by receiving light of the second wavelength reflected by the object radiated by the second light source 312b.

Referring to FIG. 4, the pulse wave sensor 110c according to an embodiment may include a light source assembly 410a and two or more photodetectors 420a and 420b. In this case, the light source assembly 410 and a first photodetector 420a may form a first channel, and the light source assembly 410 and a second photodetector 420b may form a second channel.

The light source assembly 410 may include a first light source 411 configured to emit light of a first wavelength toward an object of interest, and a second light source 412 configured to emit light of a second wavelength toward the object. In this case, the first wavelength may be a red wavelength and the second wavelength may be an infrared wavelength.

In FIG. 4, the light source assembly 410 includes two light sources, which is merely for convenience of description, but is not limited thereto. That is, the light source assembly 410 may further include one or more light sources configured to emit light of a different wavelength (e.g., blue wavelength, green wavelength, or the like) from those of the first light source 411 and the second light source 412.

The first photodetector 420a may measure a first pulse wave signal of the first channel by receiving light of the first wavelength reflected by the object radiated by the first light source 411, and measure a second pulse wave signal of the first channel by receiving light of the second wavelength reflected by the object radiated by the second light source 412.

The second photodetector 420b may measure a first pulse wave signal of the second channel by receiving light of the first wavelength reflected by the object radiated by the first light source 411, and measure a second pulse wave signal of the second channel by receiving light of the second wavelength reflected by the object radiated by the second light source 412.

The embodiments of the pulse wave sensor for measuring a pulse wave signal of the object of interest via a plurality of channels have been described with reference to FIGS. 2 to 4. However, these embodiments are merely examples and the present disclosure is not limited thereto, such that the numbers and arrangements of the light sources of the light source assemblies and the photodetectors may vary according to the utilization purpose of the pulse wave sensor and the size and shape of an electronic device in which the pulse wave sensor is mounted.

Referring to FIG. 1, the pressure sensor 120 may measure a contact pressure signal corresponding to a contact pressure between the object of interest and the pulse wave sensor 110. According to an embodiment, the pressure sensor 120 may measure a contact force signal corresponding to a contact force between the object of interest and the pulse wave sensor 110, and acquire a contact pressure signal by dividing the measured contact force by a predetermined area. The predetermined area may be a default value stored in advance in the apparatus 100 for measuring a bio-signal. According to an embodiment, the pressure sensor 120 may measure the contact force signal and a contact area signal corresponding, respectively, to a contact force and a contact area between the object of interest and the pulse wave sensor 110 and acquire the contact pressure signal by dividing the measured contact force by the measured contact area. To this end, the pressure sensor 120 may include a force sensor, an atmospheric pressure sensor, an acceleration sensor, a piezoelectric film, a load cell, a radar, a strain gauge, a contact area sensor, and the like.

The processor 130 may control an overall operation of the apparatus 100 for measuring a bio-signal and may be configured as one or more processors, may be configured with a memory, or a combination thereof.

Based on the object of interest contacting the pulse wave sensor 110, the processor 130 may control the pulse wave sensor 110 to measure a pulse wave signal of the object of interest via a plurality of channels, and may control the pressure sensor 120 to measure a contact pressure signal corresponding to a contact pressure between the object and the pulse wave sensor 110.

According to an embodiment, the processor 130 may drive each of the light sources of the pulse wave sensor 110 in a time-division manner. In this case, light source driving conditions, such as the emission time, driving order, intensity of a current, pulse duration, and the like, of each of the light sources of the pulse wave sensor 110 may be set in advance. The processor 130 may control the driving of each light source of the pulse wave sensor 110 based on the light source driving conditions.

The processor 130 may generate guide information for inducing an increase or decrease of a contact pressure between the object of interest and the pulse wave sensor 120 based on the measured contact pressure signal, and provide the guide information to the user via an output interface. For example, the processor 130 may generate guide information showing both a target pressure and the measured contact pressure, and provide the guide information to the user via the output interface. In another example, the processor 130 may compare the measured contact pressure with the target pressure, generate guide information for inducing a decrease of the contact pressure when the measured contact pressure is greater than the target pressure, generate guide information for inducing an increase of the contact pressure when the measured contact pressure is less than the target pressure, and then output the generated guide information to the user via the output interface. In this case, the target pressure signal may be preset to a value that linearly increases or decreases and may be stored in the apparatus 100 for measuring a bio-signal. The output interface may include various output interface, such as a visual output interface, an audible output interface, and a tactile output interface.

The processor 130 may analyze the measured pulse wave signal of each channel, and determine oxygen saturation of each channel. According to an embodiment, the processor 130 may analyze the pulse wave signal of each channel, determine an AC component and a DC component of each pulse wave signal, and determine oxygen saturation of each channel based on the AC component and DC component of each pulse wave signal. For example, the processor 130 may determine oxygen saturation of each channel using Equation 1 shown below.

$$r_i = \frac{AC_{red,i}/DC_{red,i}}{AC_{IR,i}/DC_{IR,i}}, SpO_{2_i} = 110 - 25 \times r_i \quad \text{(Equation 1)}$$

Referring to Equation 1, i denotes a channel index, $AC_{red,i}$ denotes an AC component of a pulse wave signal measured by using red light of channel i, $DC_{red,i}$ denotes a DC component of a pulse wave signal measured by using red light of channel i, $AC_{IR,i}$ denotes an AC component of a pulse wave signal measured by using infrared light of channel i, $DC_{IR,i}$ denotes a DC component of a pulse wave signal measured using infrared light of channel i, and $SpO_{2_i}$ denotes oxygen saturation of channel i.

The AC components and DC components of the pulse wave signal are as shown in FIG. 5.

The processor 130 may select a channel to be used in estimating a bio-signal from among the plurality of channels based on the determined oxygen saturation of each channel.

When an optical path of a pulse wave signal in one of the plurality of channels passes through a large artery, the oxygen saturation is high at a point at which an amplitude of the pulse wave signal is maximum (e.g., a point at which an AC component of the pulse wave signal is maximum), which is a point at which the change in blood vessel volume is maximum, and after the point, the blood vessel volume decreases as an external pressure of the blood vessel increases, so that the oxygen saturation decreases. Therefore, the processor 130 may select a channel for estimating bio-information based on the amount of determined oxygen saturation for each channel and/or a change in the amount thereof.

According to an embodiment, the processor 130 may determine a point at which an amplitude of the pulse wave signal is maximum (e.g., a point at which the AC component of the pulse wave signal is maximum) for each channel and may select, as a channel to be used in estimating bio-information, a channel in which a decrease of oxygen saturation occurs from the determined point for a predetermined period of time and the amount of decrease is the greatest. For example, assuming that, as shown in FIG. 6, a point at which the amplitude of the pulse wave signal is maximum ("maximum point") in channel 1 is P1, a maximum point in channel 2 is P2, a maximum point in channel 3 is P3, and a maximum point in channel 4 is P4, channel 3 and channel 4 are the channels in which the oxygen saturation decreases, for a predetermined period of time, from the maximum point at which the amplitude of the pulse wave signal is maximum, and the amount of decrease of oxygen saturation in channel 3 is greater than that in channel 4. Thus, the processor 130 may select channel 3 as a channel to be used in estimating bio-information.

According to an embodiment, the processor 130 may determine a point at which the amplitude of the pulse wave signal is maximum (e.g., a point at which the AC component of the pulse wave signal is maximum) for each channel and may select, as a channel to be used in estimating bio-information, a channel having the greatest oxygen saturation within a predetermined period time interval associated with the corresponding point from among the plurality of channels. For example, assuming that, as shown in FIG. 7, a point at which the amplitude of the pulse wave signal is maximum ("maximum point") in channel 1 is P1, a maximum point in channel 2 is P2, a maximum point in channel 3 is P3, and a maximum point in channel 4 is P4, channel 4 is a channel in which the oxygen saturation is the greatest within a predetermined time interval (e.g., an interval from time −t0 of a point at which the amplitude of the pulse wave signal is maximum to time +t0 of a point at which the amplitude of the pulse wave signal is maximum) associated with a point at which the amplitude of the pulse wave signal is maximum. Therefore, the processor 130 may select channel 4 as a channel to be used in estimating bio-information. In this case, the greatest oxygen saturation may indicate that the maximum value of oxygen saturation is the greatest or that an average value of oxygen saturation is the greatest, and the like.

In another example, the processor 130 may determine a time interval that corresponds to a predetermined contact pressure interval based on the measured contact pressure signal and select a channel having the greatest oxygen saturation within the time interval from among the plurality of channels as a channel to be used in estimating bio-information. For example, as shown in FIG. 8, the processor 130 may determine a time interval 720 that corresponds to a predetermined contact pressure interval 710. In FIG. 8, a channel having the greatest oxygen saturation in the time interval 720 is channel 4. Thus, the processor 130 may select channel 4 as a channel to be used in estimating bio-information.

Based on the channel to be used in estimating bio-information being selected, the processor 130 may estimate bio-information of the object of interest using the pulse wave signal measured via the selected channel. In this case, the bio-information may include blood pressure, vascular age, degree of arteriosclerosis, vascular compliance, blood sugar, blood triglyceride, cardiac output, total peripheral resistance, and the like.

Hereinafter, for convenience of description, a case in which the bio-information is blood pressure will be described as an example.

The processor 130 may estimate blood pressure of the object of interest based on the pulse wave signal measured via the selected channel and the measured contact pressure signal. Blood pressure may include diastolic blood pressure (DBP), systolic blood pressure (SBP), and mean arterial pressure (MAP), and the contact pressure exerted on the object of interest may act as an external pressure on a blood vessel. When the contact pressure is less than the MAP, the elastic restoring force of tissues acts in a direction of compressing the blood vessel and thereby the amplitude of the pulse wave signal is reduced. When the contact pressure becomes equal to the MAP, the elastic restoring force of tissues becomes zero and thus does not affect the blood vessel so that the amplitude of the pulse wave signal is maximized. In addition, when the contact pressure is greater than the MAP, the elastic restoring force of tissues acts in a direction of expanding the blood vessel, so that the amplitude of the pulse wave signal is reduced. Therefore, the processor 130 may analyze a change in a pulse wave signal in accordance with the change in contact pressure, and may estimate that a contact pressure obtained when the amplitude of the pulse wave signal reaches a maximum is a MAP. In addition, the processor 130 may estimate that a contact pressure obtained at a point at which an amplitude corresponds to a first proportion (e.g., 0.6) of the maximum amplitude is SBP, and estimate that a contact pressure obtained at a point at which an amplitude corresponds to a second proportion (e.g., 0.7) of the maximum amplitude is DBP.

Figure 9:
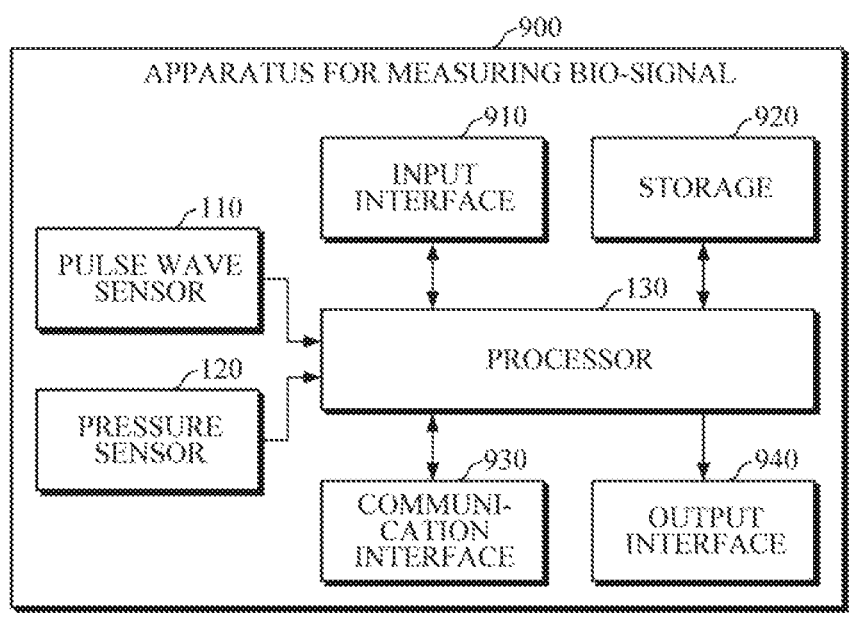
FIG. 9 is a diagram illustrating an apparatus for measuring a bio-signal according to an embodiment.

FIG. 9 is a diagram illustrating an apparatus for measuring a bio-signal according to an embodiment.

Referring to FIG. 9, the apparatus 900 for measuring a bio-signal may include a pulse wave sensor 110, a pressure sensor 120, a processor 130, an input interface 910, a storage 920, a communication interface 930, and an output interface 940. Here, the pulse wave sensor 110, the pressure sensor 120, and the processor 130 may be substantially the same as those described with reference to FIGS. 1 to 8, and hence detailed descriptions thereof might not be reiterated.

The input interface 910 may receive various operation signals from a user based on a user input. According to an embodiment, the input interface 910 may include a key pad, a dome switch, a touch pad (e.g., a resistive touch pad, a capacitive touch pad, etc.), a jog wheel, a jog switch, a hardware button, and the like. In particular, when a touchpad has a layered structure with a display, this structure may be referred to as a touch screen.

A program or instructions for operation of the apparatus 900 for measuring a bio-signal may be stored in the storage 920, and data input to the apparatus 900 for measuring a bio-signal, data processed by the apparatus 900, data for data processing by the apparatus 900, and data output by the apparatus 900 may also be stored in the storage 920. The storage 920 may include a storage medium of at least one type of flash memory type, hard disk type, multimedia card micro type, card-type memory (e.g., secure digital (SD) or extreme digital (XD) memory), random access memory (RAM), static random access memory (SRAM), read only memory (ROM), electrically erasable programmable read only memory (EEPROM), programmable read only memory (PROM), magnetic memory, magnetic disk, optical disk, and the like. In addition, the apparatus 900 for measuring a bio-signal may communicate with an external storage medium, such as web storage providing a storage function of the storage 920 via the Internet.

The communication interface 930 may communicate with an external device. For example, the communication interface 930 may transmit data input to, data stored by, and data processed by the apparatus 900 to the external device, or receive data to select a channel and/or to estimate bio-information from the external device.

In this case, the external device may be medical equipment which uses the data input to, the data stored by, and the data processed by the apparatus 900, or may be a printer or a display device for outputting results. In addition, the external device may be a digital television (TV), a desktop computer, a mobile phone, a smartphone, a tablet computer, a notebook computer, a PDA, a PMP, a navigation device, an MP3 player, a digital camera, a wearable device, or the like, but is not limited thereto.

The communication interface 930 may communicate with the external device using Bluetooth, Bluetooth low energy (BLE), near field communication (NFC), wireless local area network (WLAN) communication, ZigBee communication, infrared data association (IrDA) communication, wireless fidelity (Wi-Fi) direct (WFD) communication, ultra-wideband (UWB) communication, Ant+ communication, Wi-Fi communication, radio-frequency identification (RFID) communication, third generation (3G) communication, fourth generation (4G) communication, fifth generation (5G) communication, and the like. However, these are merely examples, and the embodiment is not limited thereto.

The output interface 940 may output the data input to, the data stored by, and the data processed by the apparatus 900. According to an embodiment, the output interface 940 may output the data input to, the data stored by, and the data processed by the apparatus 900 using various methods, such as an audible method, a visual method, and a tactile method. In this case, the output interface 940 may include a display, a speaker, a vibrator, and the like.

Figure 10:
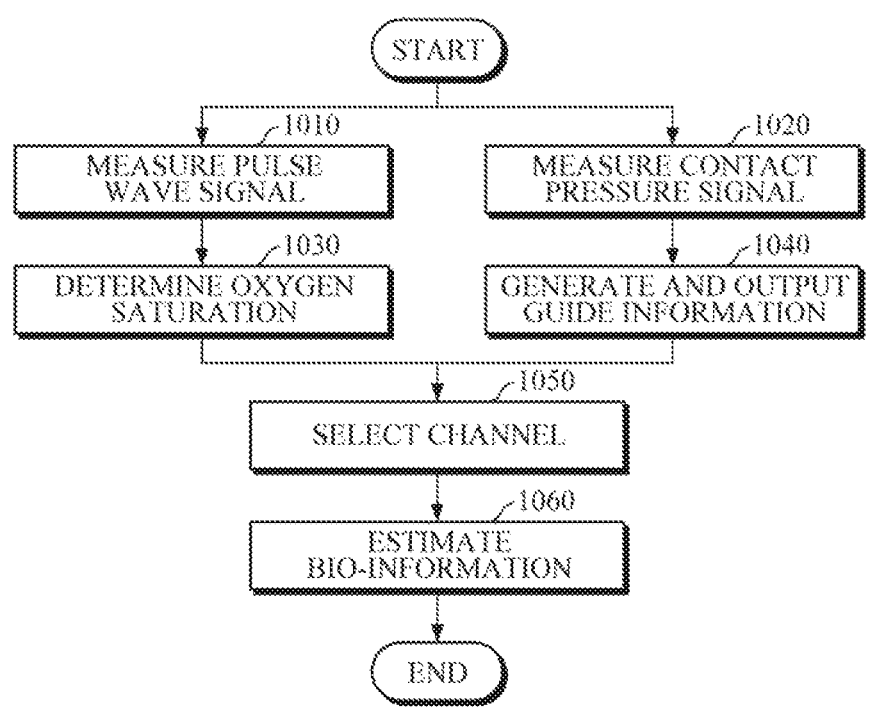
FIG. 10 is a flowchart illustrating a method of measuring a bio-signal according to an embodiment.

FIG. 10 is a flowchart illustrating a method of measuring a bio-signal according to an embodiment. The method of FIG. 10 may be performed by the apparatus 100 or 900 of FIG. 1 or 9 to measure a bio-signal.

Referring to FIG. 10, the apparatus for measuring a bio-signal may measure a pulse wave signal of an object of interest via a plurality of channels (S1010). The pulse wave signal may be a PPG signal. For example, when the object of interest contacts the pulse wave sensor, the apparatus may emit light toward the object via the plurality of channels and measure the pulse wave signal of the object by receiving light reflected by or scattered from the object. In this case, the channel may be formed by a combination of a light source assembly and a photodetector, and the light source assembly may include at least two light sources configured to emit light of different wavelengths. For example, the light source assembly may include a red light source and an infrared light source.

The apparatus for measuring a bio-signal may measure a contact pressure signal corresponding to a contact pressure between the object of interest and the pulse wave sensor (S1020). For example, the apparatus may measure a contact force signal corresponding to a contact force between the object and the pulse wave sensor, and obtain the contact pressure signal by dividing the contact force by a predetermined area. In another example, the apparatus for measuring a bio-signal may measure a contact force signal and a contact area signal corresponding to, respectively, a contact force and a contact area between the object of interest and the pulse wave sensor and obtain the contact pressure signal by dividing the measured contact force by the measured contact area.

The apparatus for measuring a bio-signal may determine oxygen saturation for each channel by analyzing the measured pulse wave signal of each channel (S1030). According to an embodiment, the apparatus may analyze the pulse wave signal of each channel to determine an AC component and a DC component of each pulse wave signal, and may determine oxygen saturation of each channel based on the AC component and DC component of each pulse wave signal. For example, the apparatus may determine the oxygen saturation of each channel using Equation 1 as shown elsewhere herein.

The apparatus for measuring a bio-signal may generate and output guide information for inducing an increase or decrease of a contact pressure between the object of interest and the pulse wave sensor based on the measured contact pressure signal (S1040). For example, the apparatus may generate and output guide information showing both a target pressure and the measured contact pressure, or may compare the measured contact pressure with a target pressure, generate guide information for inducing a decrease of the contact pressure based on the measured contact pressure being greater than the target pressure, generate guide information for inducing an increase of the contact pressure based on the measured contact pressure being less than the target pressure, and then may output the generated guide information via an output interface.

The apparatus for measuring a bio-signal may select a channel to be used in estimating bio-information from among the plurality of channels based on the determined oxygen saturation for each channel (S1050).

For example, the apparatus for measuring a bio-signal may determine a point at which an amplitude of the pulse wave signal is maximum (e.g., a point at which the AC component of the pulse wave signal is maximum) for each channel, and may select, as a channel to be used in estimating bio-information, a channel in which a decrease of oxygen saturation occurs from the determined point for a predetermined period of time and the amount of decrease is the greatest from among the plurality of channels. In another example, the apparatus for measuring a bio-signal may determine a point at which the amplitude of the pulse wave signal is maximum (e.g., a point at which the AC component of the pulse wave signal is maximum) for each channel, and may select a channel having the greatest oxygen saturation within a predetermined time interval associated with the determined point as a channel to be used in estimating bio-information from among the plurality of channels. In still another example, the apparatus for measuring a bio-signal may determine a time interval that corresponds to a predetermined contact pressure interval on the basis of the measured contact pressure signal and select, from among the plurality of channels, a channel having the greatest oxygen saturation within the time interval as a channel to be used in estimating bio-information.

Based on the channel to be used in estimating bio-information being selected, the apparatus for measuring a bio-signal may estimate bio-information of the object of interest using the pulse wave signal measured via the selected channel (S1060). In this case, the bio-information may include blood pressure, vascular age, degree of arteriosclerosis, vascular compliance, blood sugar, blood triglyceride, cardiac output, total peripheral resistance, and the like. According to an embodiment, the apparatus may estimate blood pressure of the object of interest based on the pulse wave signal measured via the selected channel and the measured contact pressure signal. For example, the apparatus may analyze a change of the pulse wave signal in accordance with a change in contact pressure, estimate that a contact pressure obtained at a point at which the amplitude corresponds to a first proportion (e.g., 0.6) of the maximum amplitude is SBP, and estimate that a contact pressure obtained at a point at which the amplitude corresponds to a second proportion (e.g., 0.7) of the maximum amplitude is DBP.

Figure 11:
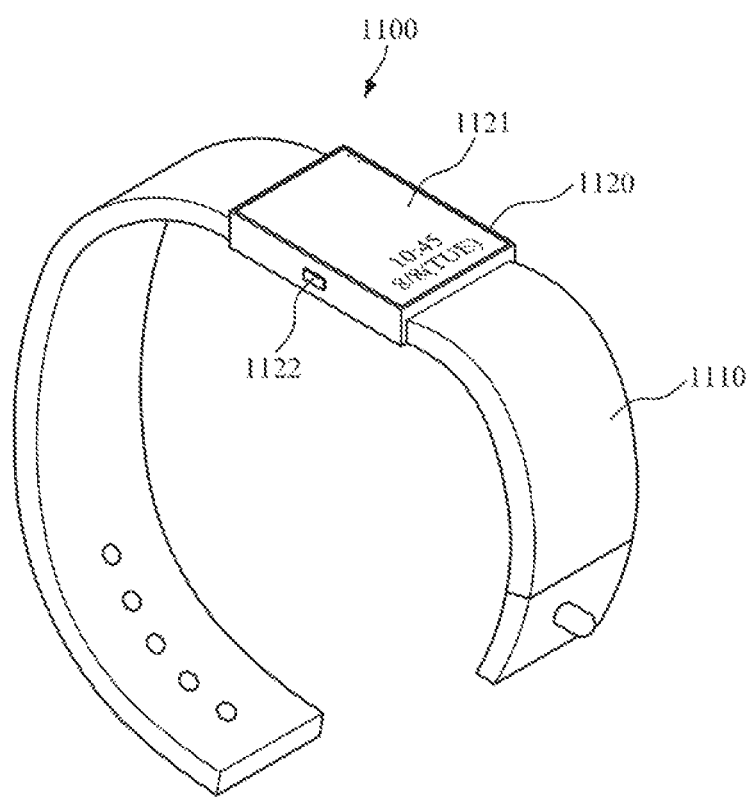
FIG. 11 is a perspective view of a wrist-type wearable device according to an embodiment.

FIG. 11 is a perspective view of a wrist-type wearable device.

Referring to FIG. 11, the wrist-type wearable device 1100 may include a strap 1110 and a main body 1120.

The strap 1110 may be configured with a plurality of strap members each of which is formed to be bent to wrap around a wrist of a user. However, this is merely an example, and the embodiment is not limited thereto. That is, the strap 1110 may be configured in the form of a flexible band.

The main body 1120 may include the above-described apparatus 100 or 900 for measuring a bio-signal mounted therein. In addition, a battery for supplying power to the wrist-type wearable device 1100 and the apparatus 100 or 900 for measuring a bio-signal may be embedded in the main body 1120.

A pulse wave sensor may be mounted on a lower part of the main body 1120 in such a manner to be exposed to the wrist of the user. Accordingly, when the user wears the wrist-type wearable device 1100, the pulse wave sensor may contact the user's skin. In this case, the pulse wave sensor may emit light toward an object of interest and measure a pulse wave signal of the object by receiving light reflected by or scattered from the object.

The wrist-type wearable device 1100 may further include an input interface 1121 and a display 1122, which are mounted in the main body 1120. The input interface 1121 may receive various operation signals from the user based on a user input. The display 1122 may display data processed by the wrist-type wearable device 1100 and the apparatus 100 or 900 for measuring a bio-signal, processing result data, and the like.

The current embodiments can be implemented as computer readable code stored in a non-transitory computer-readable medium. Code and code segments constituting the computer program can be inferred by a skilled computer programmer in the art. The computer-readable medium includes all types of recording media in which computer readable data are stored. Examples of the computer-readable medium include a ROM, a RAM, a CD-ROM, a magnetic tape, a floppy disk, and an optical data storage. Further, the computer-readable medium may be implemented in the form of a carrier wave such as Internet transmission. In addition, the computer-readable medium may be distributed to computer systems via a network, in which computer readable code may be stored and executed in a distributed manner.

A number of examples have been described above. However, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating bio-information of an object of interest comprising:
a processor configured to:
obtain a plurality of pulse wave signals of an object via a plurality of channels;
determine a plurality of oxygen saturation values corresponding to the plurality of channels based on the plurality of pulse wave signals;
select a channel to be used for estimating the bio-information of the object of interest from among the plurality of channels based on the plurality of oxygen saturation values; and
estimate the bio-information of the object of interest based on a pulse wave signal corresponding to the selected channel.

2. The apparatus of claim 1, further comprising:
a pulse wave sensor comprising one or more light source assemblies each configured to emit light of at least two different wavelengths toward the object of interest, and two or more photodetectors configured to measure the plurality of pulse wave signals by receiving light reflected by the object of interest.

3. The apparatus of claim 1, further comprising:
a pulse wave sensor comprising two or more light source assemblies each configured to emit light of at least two different wavelengths toward the object of interest, and one or more photodetectors configured to measure the plurality of pulse wave signals by receiving light reflected by the object of interest.

4. The apparatus of claim 1, wherein each of the plurality of channels includes a light source assembly configured to emit light of at least two different wavelengths toward the object of interest and a photodetector configured to measure the plurality of pulse wave signals by receiving light reflected by the object of interest.

5. The apparatus of claim 4, wherein the at least two wavelengths include a red wavelength and an infrared wavelength.

6. The apparatus of claim 1, wherein the processor is configured to:
determine an alternating current (AC) component and a direct current (DC) component of each of the plurality of pulse wave signals; and determine the plurality of oxygen saturation values corresponding to the plurality of channels based on the determined AC component and DC components.

7. The apparatus of claim 1, wherein the processor is further configured to:
determine, for each channel, a point at which an amplitude of a respective pulse wave signal is maximum; and
select, as the channel to be used for estimating the bio-information, the channel in which a decrease of oxygen saturation occurs from the determined point for a predetermined period of time and in which an amount of decrease in oxygen saturation is the greatest from among the plurality of channels.

8. The apparatus of claim 1, wherein the processor is further configured to:
determine, for each channel, a point at which an amplitude of a respective pulse wave signal is maximum; and
select, from among the plurality of channels, the channel having the greatest oxygen saturation within a predetermined time interval associated with the determined point as the channel to be used for estimating the bio-information.

9. The apparatus of claim 1, further comprising:
a pressure sensor configured to measure a contact pressure signal corresponding to a contact pressure between the object of interest and a pulse wave sensor,
wherein the processor is further configured to:
determine a time interval that corresponds to a predetermined contact pressure interval based on the measured contact pressure signal; and
select, from among the plurality of channels, the channel having the greatest oxygen saturation within the time interval as the channel to be used for estimating the bio-information.

10. The apparatus of claim 1, further comprising:
a pressure sensor configured to measure a contact pressure signal corresponding to a contact pressure between the object of interest and a pulse wave sensor,
wherein the processor is further configured to generate guide information for inducing an increase or decrease of the contact pressure between the object of interest and the pulse wave sensor based on the measured contact pressure signal.

11. The apparatus of claim 1, wherein the bio-information includes at least one of blood pressure, vascular age, degree of arteriosclerosis, vascular compliance, blood sugar, blood triglyceride, cardiac output, and total peripheral resistance.

12. The apparatus of claim 1, further comprising:
a pressure sensor configured to measure a contact pressure signal corresponding to a contact pressure between the object of interest and the pulse wave sensor,
wherein the processor is further configured to estimate blood pressure of the object of interest based on the pulse wave signal corresponding to the selected channel and the measured contact pressure signal.

13. A method of estimating bio-information of an object of interest, the method comprising:
measuring a plurality of pulse wave signals of the object of interest via a plurality of channels;
determining a plurality of oxygen saturation values corresponding to the plurality of channels based on the measured plurality of pulse wave signals;
selecting a channel to be used for estimating the bio-information from among the plurality of channels based on the plurality of oxygen saturation values; and
estimating the bio-information of the object based on a pulse wave signal corresponding to the selected channel.

14. The method of claim 13, wherein the determining of the plurality of oxygen saturation values comprises determining an alternating current (AC) component and a direct current (DC) component of each of the plurality of pulse wave signals and determining the plurality of oxygen saturation values based on the determined AC component and DC components.

15. The method of claim 13, wherein the selecting of the channel to be used for estimating the bio-information from among the plurality of channels comprises determining, for each channel, a point at which an amplitude of a respective pulse wave signal is maximum and selecting, as the channel to be used for estimating the bio-information, the channel in which a decrease of oxygen saturation occurs from the determined point for a predetermined period of time and an amount of decrease is the greatest from among the plurality of channels.

16. The method of claim 13, wherein the selecting of the channel to be used for estimating bio-information from among the plurality of channels comprises determining, for each channel, a point at which an amplitude of the pulse wave signal is maximum and selecting, as the channel to be used for estimating the bio-information, the channel having the greatest oxygen saturation within a predetermined time interval associated with the determined point from among the plurality of channels.

17. The method of claim 13, further comprising:
measuring a contact pressure signal corresponding to a contact pressure between the object of interest and a pulse wave sensor,
wherein the selecting of the channel to be used for estimating the bio-information from among the plurality of channels comprises determining a time interval that corresponds to a predetermined contact pressure interval based on the measured contact pressure signal and selecting the channel having the greatest oxygen saturation within the time interval from among the plurality of channels.

18. The method of claim 13, further comprising:
measuring a contact pressure signal corresponding to a contact pressure between the object of interest and a pulse wave sensor; and
generating guide information for inducing an increase or decrease of the contact pressure between the object of interest and the pulse wave sensor based on the measured contact pressure signal.

19. The method of claim 13, wherein the bio-information includes at least one of blood pressure, vascular age, degree of arteriosclerosis, vascular compliance, blood sugar, blood triglyceride, cardiac output, and total peripheral resistance.

20. The method of claim 13, further comprising:
measuring a contact pressure signal corresponding to a contact pressure between the object of interest and a pulse wave sensor; and
estimating blood pressure of the object of interest based on the pulse wave signal measured via the selected channel and the measured contact pressure signal.

* * * * *